(12) United States Patent
Becker et al.

(10) Patent No.: US 8,100,124 B2
(45) Date of Patent: Jan. 24, 2012

(54) DEVICE WITH A RESPIRATOR AND A HUMIDIFIER

(75) Inventors: Uwe Becker, Eichenau (DE); Karsten Dieckmann, Lübeck (DE); Jochim Koch, Ratzeburg (DE); Thomas Krüger, Reinfeld (DE); Hans-Wilhelm Steen, Zarpen (DE)

(73) Assignee: Dräger Medical GmbH, Lübeck (DE)

( * ) Notice: Subject to any disclaimer, the term of this patent is extended or adjusted under 35 U.S.C. 154(b) by 1166 days.

(21) Appl. No.: 11/832,947

(22) Filed: Aug. 2, 2007

(65) Prior Publication Data

US 2008/0072904 A1    Mar. 27, 2008

(30) Foreign Application Priority Data

Sep. 27, 2006   (DE) .................. 10 2006 045 739

(51) Int. Cl.
*A61M 16/00* (2006.01)
*A62B 7/00* (2006.01)

(52) U.S. Cl. .......... 128/204.21; 128/203.12; 128/204.18

(58) Field of Classification Search .......... 128/200.11–200.13, 200.24, 203.12, 128/203.16, 204.13, 204.14, 204.18, 204.21
See application file for complete search history.

(56) References Cited

U.S. PATENT DOCUMENTS

| | | | |
|---|---|---|---|
| 7,677,246 B2 * | 3/2010 | Kepler et al. | 128/204.18 |
| 2003/0111080 A1 * | 6/2003 | Olsen et al. | 128/207.11 |
| 2004/0182386 A1 * | 9/2004 | Meier | 128/203.12 |
| 2004/0187871 A1 * | 9/2004 | Kimmel et al. | 128/204.23 |
| 2006/0191531 A1 * | 8/2006 | Mayer et al. | 128/200.11 |
| 2008/0072900 A1 * | 3/2008 | Kenyon et al. | 128/204.18 |

FOREIGN PATENT DOCUMENTS

EP    0 274 996 B1    7/1988

* cited by examiner

*Primary Examiner* — Justine Yu
*Assistant Examiner* — Valerie L Skorupa
(74) *Attorney, Agent, or Firm* — McGlew and Tuttle, P.C.

(57) ABSTRACT

A device with a respirator (1) and with a humidifier (11) for breathing gas. Breathing gas humidification is adapted to the different operating states of the respirator (1). A connection (13) is provided for bidirectional data transmission between the control and operating unit (8) of the respirator (1) and the control and operating unit (9) of the humidifier (11).

15 Claims, 1 Drawing Sheet

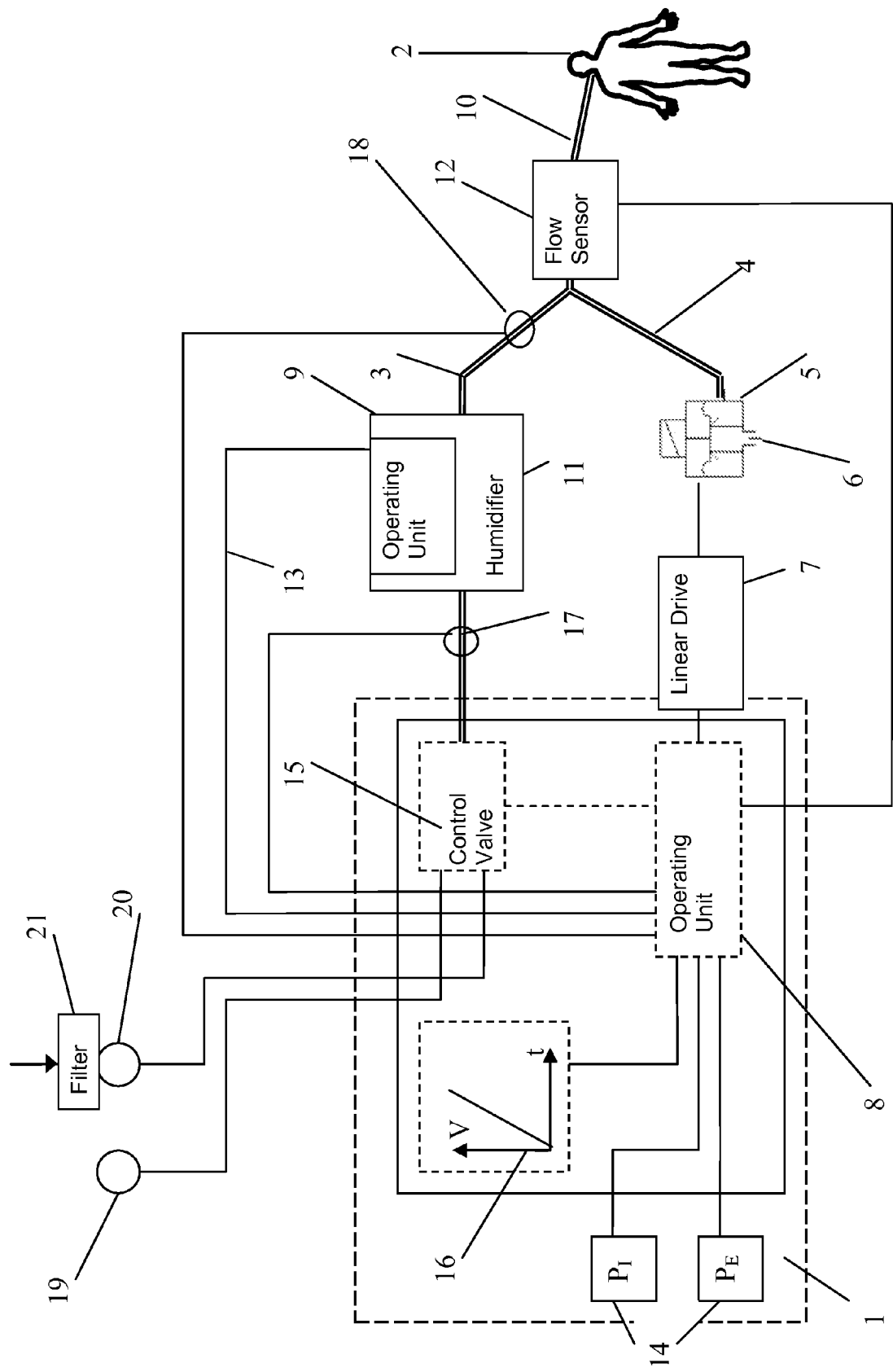

DEVICE WITH A RESPIRATOR AND A HUMIDIFIER

CROSS REFERENCE TO RELATED APPLICATIONS

This application claims the benefit of priority under 35 U.S.C. §119 of German Patent Application DE 10 2006 045 739.0 filed Sep. 27, 2006, the entire contents of which are incorporated herein by reference.

FIELD OF THE INVENTION

The present invention pertains to a device with a respirator (also known as a ventilator) and a humidifier.

BACKGROUND OF THE INVENTION

Patients who are artificially respirated over a rather long period of time must receive humidified and temperature-controlled breathing gas. A humidifier, which increases the concentration of water vapor in the gas to be breathed in and heats it to a suitable temperature, is arranged in the inspiration line for this purpose.

A respirator with a humidifier appears, for example, from EP 274 996 B1. The humidifier is arranged in the inspiration line of the respirator. Water is heated with a heating device to the extent that it can be mixed as water vapor with the inhaled gas. The heating device is connected to a control device, and the control device additionally detects the temperature of the inhaled gas in the vicinity of the patient by means of a temperature sensor. The humidifier and the respirator are separate components, which do not exchange any information.

If settings are changed on the respirator, corresponding adaptations must also be made mostly on the control device of the humidifier. Setting the humidifier such that a breathing gas humidity and breathing gas temperature that are suitable for the patient are sent without condensation of water occurring or without the gas mixture containing too little moisture for the patient depends on the user's experience.

SUMMARY OF THE INVENTION

The basic object of the present invention is to improve a device of the type such that a breathing gas humidification adapted to the different operating states of the respirator is achieved.

According to the invention, a respiration device is provided comprising a respirator and a humidifier for humidifying breathing gas. A first operating and control unit is provided for controlling operation of the respirator. A second control and operating unit is provided at the humidifier. A connection means provides data transmission between the first operating and control unit and the second control and operating unit.

The connection means may advantageously have additional means for transmitting electric energy.

The data transmission may advantageously include the first operating and control unit transferring data to the second control and operating unit via the connection means including inspiratory gas flow data, inspiratory oxygen concentration data, inspiratory gas temperature data and the mode of operation of the respirator data.

The respirator may advantageously include a means for operating the humidifier as well as for displaying and outputting status and alarm reports of the humidifier.

The logistic connection of the humidifier to the control and operating unit has the advantage that the change in settings on the respirator is passed on directly to the control and operating unit of the humidifier and that, in the reverse case, the control and operating unit of the respirator receives all operating and status data of the humidifier.

If the gas flow from the respirator to the patient is briefly stopped, for example, during an suction maneuver, the humidifier is also deactivated during this period, so that condensation of water will not occur in the inspiration tube. The data communication between the control and operating unit of the respirator and that of the humidifier of the connection means may take place via a data line or in a wireless manner by means of radio or infrared light. There preferably is a bidirectional data connection, so that the setting data of the humidifier are also displayed on the operating unit of the respirator and, conversely, information on measured values and setting data of the respirator reach the control and operating unit of the humidifier.

The data to be transmitted from the respirator to the humidifier are preferably the inspiratory gas flow, the inspiratory oxygen concentration, the inspiratory gas temperature and the mode of operation of the respirator. Concerning the mode of operation, distinction is to be made between a so-called blower operation, operation with central gas supply and combinations of blower operation and operation with central gas supply. Breathing gas is drawn in directly from the environment via a filter in case of the blower operation. By contrast, the breathing gas is taken from a central gas supply unit in case of operation with central gas supply. When gas is taken from the environment, the breathing gas already has a certain moisture content, so that the humidifier output can be reduced, whereas dry gases are to be humidified when the gas is taken from the central gas supply unit.

An exemplary embodiment of the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWINGS

In the drawings:

The only FIGURE is a schematic diagram showing a respirator for supplying a patient with breathing gas.

DESCRIPTION OF THE PREFERRED EMBODIMENT

Referring to the drawings in particular, the only figure shows a respirator for supplying a patient 2 with breathing gas via an inspiration line 3. Via an expiration line 4 and a Positive End Expiratory Pressure (PEEP) valve 5, the gas breathed out reaches an expiration outlet 6, which sets an expiration pressure $P_E$ at the patient 2 during expiration. The PEEP valve 5 is actuated by a linear drive 7, which is connected to a first control and operating unit 8 of the respirator. The inspiration line 3 and the expiration line 4 unite in a Y-piece, from which a breathing gas line 10 common for the inspiration and expiration leads to the patient 2. A humidifier 11 and a breathing gas flow sensor 12 for measuring the breathing gas flow V are arranged in the inspiration line 3. In addition, an oxygen sensor 17 measures the inspiratory oxygen concentration and a temperature sensor 18 detects the inspiratory breathing gas temperature. The phases of breathing are controlled by means of a breathing flow control valve 15. Set point adjusters 14 for the inspiration pressure pi and the expiration pressure $P_E$, which can be set by the user to preselected values, are connected to the first control and operating unit 8. The breathing flow control valve 15 is connected to a pressurized gas source 19, and the breathing flow control valve 15 receives preset values from a ramp generator 16 during the inspiration in such a way that a preset inspiration pressure $p_I$ is present during the inspiration, and a preset expiration pressure $P_E$ is present during the expiration, together with the PEEP valve 5. As an alternative or in addition to the pressurized gas source 19, a blower 20 is provided, which draws in breathing gas from the environment via a filter 21. The breathing gas may be taken either entirely from the pressurized gas source 19, for example, oxygen and compressed air, or ambient air is drawn in with the blower 20 and oxygen is added from the pressurized gas source 19.

The humidifier 11 contains a second control and operating unit 9, which is connected via a connection cable of the first control and operating unit 8 of the respirator 1. The connection cable 13 is provided for transmitting electricity to the humidifier 11 and for bidirectional data exchange between the control and operating units 8, 9.

The device according to the present invention operates as follows.

The humidifier 11 (via second control and operating unit 9) will preferably poll the respirator 1 for the parameters inspiratory gas flow, inspiratory oxygen concentration, inspiratory gas temperature and the mode of operation of the respirator. If the communication is established via the connection means 13 between the humidifier control and operating unit (second control and operating unit 9) of the humidifier 11 and the respirator control and operating unit (first control and operating unit 8) of the respirator 1, the humidifier 11 sends an inquiry to poll the identification code of the respirator 1. The respirator 1 correspondingly identifies itself in the reply. It appears from the identification of the respirator 1 which code is to be assigned to which parameter and in what format and in which unit this parameter is to be assumed to express.

The humidifier 11 first sends reading commands with the codes of the parameters to be polled to the connected respirator 1. It appears, for example, from the reply of the respirator 1 that an oxygen concentration of 60% is currently being sent to the patient and that a blower 20 is active, which delivers a maximum pressure of 75 mbar. The humidifier 11 will now either measure the humidity of the ambient air or assume that the usual moisture content of the ambient air is at a relative humidity of approximately 50%. The gas fed to the patient thus already has a certain moisture content, so that only the moisture still missing from the breathing gas relative to the breathing gas temperature to be set must be added. The oxygen added to the ambient air from the central gas supply is assumed to be dry. Combined, the gas mixture now already has a relative humidity of about 25%. Corresponding to the settings performed, the humidifier 11 has to introduce only the residual moisture into the breathing gas, so that a relative humidity of 95% will be reached. Undesired condensation of water is prevented from occurring by taking into account the basic moisture content already present in the breathing gas.

The information that no gas is currently being released to the patient because the phase of expiration is present is sent when the connected respirator is next polled by the humidifier. The humidifier 11 determines from this information that no humidifying output is currently being needed. However, if the respirator 1 shows in the next step that a gas flow of 60 L per minute is being released to the patient, the inspiration starts and the humidifier must humidify the gas with maximum output. If the gas flow decreases during the phase of inspiration, the humidifier 11 can correspondingly adapt its humidification output and thus bring about optimal humidification of the breathing gas.

It is especially advantageous now to make settings for the humidifier 11 via the respirator operating and control unit (the first control and operating unit 8) of the respirator 1. All alarms and other reports of the humidifier are now provided as an output on the operating unit. The user can thus change the preset set point for the humidifier, for example, on the operating unit, in such a way that the humidification output is reduced from 95% relative humidity to 90% relative humidity. On the other hand, the user receives the information, via the respirator operating and control unit (the first control and operating unit 8) of the respirator 1, that the water reserve in the humidifier is depleted and must be replenished. The user can thus monitor the humidifier from a central operating unit and change settings if needed.

While specific embodiments of the invention have been shown and described in detail to illustrate the application of the principles of the invention, it will be understood that the invention may be embodied otherwise without departing from such principles.

What is claimed is:

1. A respiration device comprising:
    a respirator with respiration data acquisition means for acquiring inspiratory gas flow data and at least one of inspiratory oxygen concentration data, inspiratory gas temperature data and mode of operation of the respirator data;
    a humidifier for humidifying breathing gas;
    a first operating and control unit for controlling operation of said respirator and for acquiring data from said respiration data acquisition means;
    a second control and operating unit at said humidifier; and
    a connection means for providing bidirectional data transmission between said first operating and control unit and said second control and operating unit including transmission of inspiratory gas flow data and at least one of inspiratory oxygen concentration data, inspiratory gas temperature data and mode of operation of the respirator data from said first operating and control unit to said second control and operating unit, said first operating and control unit making settings for the humidifier by sending settings from said first operating and control unit to said second control and operating unit and monitoring the humidifier from said first operating and control unit to change settings of the humidifier by sending settings from said first operating and control unit to said second control and operating unit if needed.

2. A device in accordance with claim 1, wherein said connection means has additional means for transmitting electric energy.

3. A device in accordance with claim 1, wherein:
    said data transmission includes said first operating and control unit transferring data to said second control and operating unit via said connection means including each of said inspiratory gas flow data, said inspiratory oxygen concentration data, said inspiratory gas temperature data and said mode of operation of said respirator data; and
    said second control and operating unit changes operation of the humidifier based on changes in said data transmission.

4. A device in accordance with claim 3, further comprising:
    a gas supply connected to said breathing flow control valve; and a blower connected to said breathing flow control valve wherein said first operating and control unit controls a mode of operation of said respirator based on a blower operation with said blower, operation with said gas supply and combinations of blower operation and operation with gas supply wherein said data transmission includes respirator mode of operation data.

5. A device in accordance with claim 4, wherein:
the mode of operation data includes data related to a percentage of gas supplied from the blower and a percentage of gas supplied from the gas supply;
said blower draws breathing gas from the environment via a filter in case of the blower operation and breathing gas is taken from a central gas supply unit in case of operation with said gas supply whereby when gas is taken from the environment, the breathing gas already has a certain moisture content, so that the humidifier output is reduced, whereas dry gases are humidified when the gas is taken from the central gas supply unit; and
said second control and operating unit changes operation of the humidifier to account for moisture content based on combined blower operation and operation with said gas supply based on said data related to a percentage of gas supplied from the blower and a percentage of gas supplied from the gas supply.

6. A device in accordance with claim 1, wherein:
said data transmission includes said second control and operating unit transferring data to said first operating and control unit via said connection means including status data and alarm data; and
said respirator includes means for operating said humidifier as well as for displaying and outputting status and alarm reports of said humidifier based on said second control and operating unit transferring data to said first operating and control unit.

7. A respiration device comprising:
a breathing gas inspiration line;
a breathing gas expiration line;
a respirator with a breathing flow control for regulating a breathing gas inspiration pressure and a breathing gas expiration pressure;
a humidifier for humidifying breathing gas fed to said inspiration line;
a first operating and control unit for controlling operation of said respirator including setting breathing gas inspiration pressure and breathing gas expiration pressure;
a second control and operating unit for adapting breathing gas humidification to different operating states of the respirator based on respiration data;
a connection means providing bidirectional data transmission between said first operating and control unit and said second control and operating unit including respiration data transmission between said first operating and control unit and said second control and operating unit;
a gas flow sensor, connected to said first operating and control unit, for measuring inspiration breathing gas flow;
an oxygen sensor, connected to said first operating and control unit, for measuring inspiratory oxygen concentration; and
a temperature sensor, connected to said first operating and control unit, for measuring inspiratory breathing gas temperature, wherein said data transmission includes said first operating and control unit transferring data to said second control and operating unit via said connection means including inspiratory gas flow data, inspiratory oxygen concentration data, inspiratory gas temperature data and a mode of operation of said respirator data, said first operating and control unit making settings for the humidifier by sending settings from said first operating and control unit to said second control and operating unit and monitoring the humidifier from said first operating and control unit to change settings of the humidifier by sending settings from said first operating and control unit to said second control and operating unit if needed.

8. A device in accordance with claim 7, wherein said connection means has additional means for transmitting electric energy.

9. A device in accordance with claim 8, wherein:
said breathing gas inspiration line and said breathing gas expiration line are joined in a Y-piece with a breathing gas common line;
said gas flow sensor is connected to one of the breathing gas inspiration and the breathing gas common line for measuring inspiration breathing gas flow;
said oxygen sensor is connected to one of the breathing gas inspiration and the breathing gas common line for measuring inspiratory oxygen concentration; and
said temperature sensor is connected to one of the breathing gas inspiration and the breathing gas common line for measuring inspiratory breathing gas temperature; and
said second control and operating unit changes operation of the humidifier based on changes in said data transmission.

10. A device in accordance with claim 9, wherein:
said data transmission includes said second control and operating unit transferring data to said first operating and control unit via said connection means including status data and alarm data; and
said respirator includes means for operating said humidifier as well as for displaying and outputting status and alarm reports of said humidifier based on said second control and operating unit transferring data to said first operating and control unit.

11. A device in accordance with claim 9, further comprising:
a gas supply connected to said breathing flow control valve; and
a blower connected to said breathing flow control valve wherein said first operating and control unit controls a mode of operation of said respirator based on a blower operation with said blower, operation with said gas supply and combinations of blower operation and operation with gas supply wherein said data transmission includes respirator mode of operation data and the mode of operation data includes data related to a percentage of gas supplied from the blower and a percentage of gas supplied from the gas supply.

12. A device in accordance with claim 11, wherein:
said blower draws breathing gas from the environment via a filter in case of the blower operation and breathing gas is taken from a central gas supply unit in case of operation with said gas supply whereby when gas is taken from the environment, the breathing gas already has a certain moisture content, so that the humidifier output is reduced, whereas dry gases are humidified when the gas is taken from the central gas supply unit; and
said second control and operating unit changes operation of the humidifier to account for moisture content based on combined blower operation and operation with said gas supply based on said data related to a percentage of gas supplied from the blower and a percentage of gas supplied from the gas supply.

13. A respiration device comprising:

a breathing gas inspiration line;

a breathing gas expiration line;

a respirator with a breathing flow control valve for regulating a breathing gas inspiration pressure and a positive end expiratory pressure valve for regulating breathing gas expiration pressure;

a humidifier for humidifying inspiration breathing gas;

a first operating and control unit for controlling operation of said respirator including controlling said breathing flow control valve and controlling said positive end expiratory pressure valve;

a second control and operating unit for adapting breathing gas humidification to different operating states of the respirator;

a connection means for providing bidirectional data transmission between said first operating and control unit and said second control and operating unit including respiration data transmission between said first operating and control unit and said second control and operating unit;

a gas flow sensor for measuring inspiration breathing gas flow;

an oxygen sensor, connected to said first operating and control unit, for measuring inspiratory oxygen concentration;

a gas flow sensor, connected to said first operating and control unit, for measuring inspiration breathing gas flow;

a temperature sensor, connected to said first operating and control unit, for measuring inspiratory breathing gas temperature, wherein said data transmission includes said first operating and control unit transferring data to said second control and operating unit via said connection means including inspiratory gas flow data, inspiratory oxygen concentration data, inspiratory gas temperature data and a mode of operation of said respirator data and wherein said second control and operating unit changes operation of the humidifier based on changes in said data transmission;

a gas supply connected to said breathing flow control valve; and a blower connected to said breathing flow control valve wherein said first operating and control unit controls a mode of operation of said respirator based on a blower operation with said blower, operation with said gas supply and combinations of blower operation and operation with gas supply wherein said data transmission includes respirator mode of operation data, wherein the mode of operation data includes data related to a percentage of gas supplied from the blower and a percentage of gas supplied from the gas supply; and said blower draws breathing gas from the environment via a filter in case of the blower operation and breathing gas is taken from a central gas supply unit in case of operation with said gas supply whereby when gas is taken from the environment, the breathing gas already has a certain moisture content, and humidifier output is reduced, whereas dry gases are humidified when the gas is taken from the central gas supply unit and said second control and operating unit changes operation of the humidifier to account for moisture content based on combined blower operation and operation with said gas supply based on said data related to a percentage of gas supplied from the blower and a percentage of gas supplied from the gas supply.

14. A device in accordance with claim 13, wherein said connection means has additional means for transmitting electric energy.

15. A device in accordance with claim 13, wherein:

said data transmission includes said second control and operating unit transferring data to said first operating and control unit via said connection means including status data and alarm data; and said respirator includes means for operating said humidifier as well as for displaying and outputting status and alarm reports of said humidifier based on said second control and operating unit transferring data to said first operating and control unit, said first operating and control unit making settings for the humidifier by sending settings from said first operating and control unit to said second control and operating unit and monitoring the humidifier from said first operating and control unit to change settings of the humidifier by sending settings from said first operating and control unit to said second control and operating unit if needed.

* * * * *